United States Patent [19]

Vishnevsky et al.

[11] 4,111,206
[45] Sep. 5, 1978

[54] SURGICAL INSTRUMENT FOR APPLYING METAL STAPLES TO ORGANS AND TISSUES AND FOR SIMULTANEOUS DIVISION THEREOF

[76] Inventors: Alexandr Alexandrovich Vishnevsky, Novokuznetskaya ulitsa, 13/15, kv. 269; Ivan Alexandrovich Korolkov, Polyarnaya ulitsa, 52, korpus 2, kv. 174; Boris Andreevich Smirnov, ulitsa Borisa Galushkina, 17, kv. 26; Tatyana Lukyanovna Ivanova, Polyarnaya ulitsa, 52, korpus 3, kv. 408; Arnold Aramovich Adamian, ulitsa Kakhovka, 10/12, korpus 1, kv. 3; Galina Vladimirovna Mitkova, Novokuznetskaya ulitsa, 13/15, kv. 269, all of Moscow, U.S.S.R.

[21] Appl. No.: 681,689

[22] Filed: Apr. 29, 1976

[30] Foreign Application Priority Data

May 4, 1975 [SU] U.S.S.R. .............................. 2130062

[51] Int. Cl.² .............................................. A61B 17/32
[52] U.S. Cl. .............................. 128/305; 128/334 R; 227/19
[58] Field of Search .................. 128/305, 334 R, 335, 128/337, 305.3, 305.5, 317; 227/19; 30/108, 92.5, 347, 307, 128; 83/508

[56] References Cited

U.S. PATENT DOCUMENTS

| | | | |
|---|---|---|---|
| 1,928,718 | 10/1933 | Covey | 30/307 |
| 1,990,967 | 2/1935 | Wenzel | 30/347 |
| 3,011,257 | 12/1961 | Bamberger | 30/128 |
| 3,079,606 | 3/1963 | Bobrov et al. | 227/76 |
| 3,490,675 | 1/1970 | Green et al. | 227/19 |
| 3,701,352 | 10/1972 | Bosworth | 128/305 |

*Primary Examiner*—Robert W. Michell
*Assistant Examiner*—Michael H. Thaler
*Attorney, Agent, or Firm*—Steinberg & Blake

[57] ABSTRACT

A surgical instrument for applying sutures of metal staples comprises an elongated staple inserting jaw and an elongated clinching jaw located alongside the former. The anterior operative tip of the staple inserting jaw contains magazines with staple recesses wherein staple driving members are also located, and the anterior operative tip of the clinching jaw has anvils located opposite said magazines and having grooves for bending the tips of said staples. The advancement of the driving members within the magazine recesses and the ejection of the staples is realized with the aid of an actuating bar located alongside the staple inserting jaw and being capable of moving longitudinally, and having an inclined camming surface at the tip facing the magazines that is intended for engaging with the staple driving members. The same tip of the actuating bar, somewhat rearwardly, has a pivotally connected disk-shaped knife for cutting the organs or tissues, the operative tip of the clinching jaw opposite said knife having an exchangeable elastic lining wherein the knife cuts in the course of tissue division.

7 Claims, 8 Drawing Figures

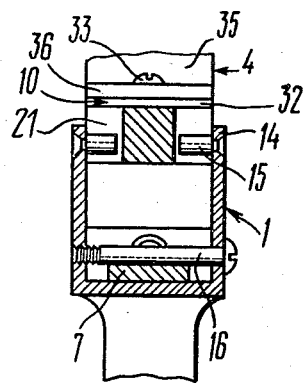
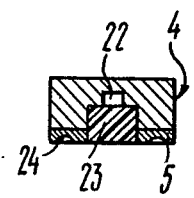
FIG. 2  FIG. 4
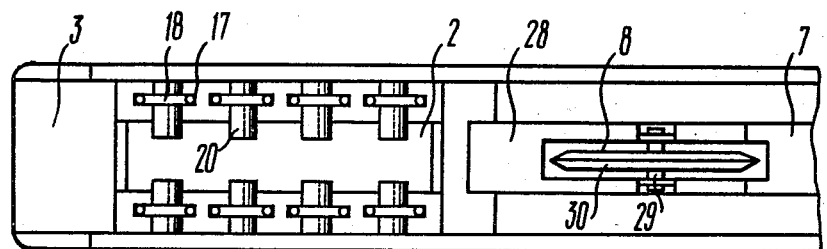
FIG. 3
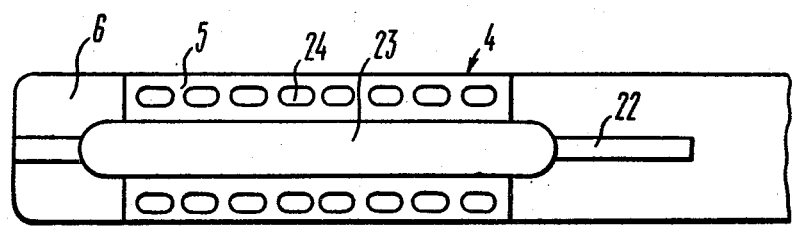
FIG. 5

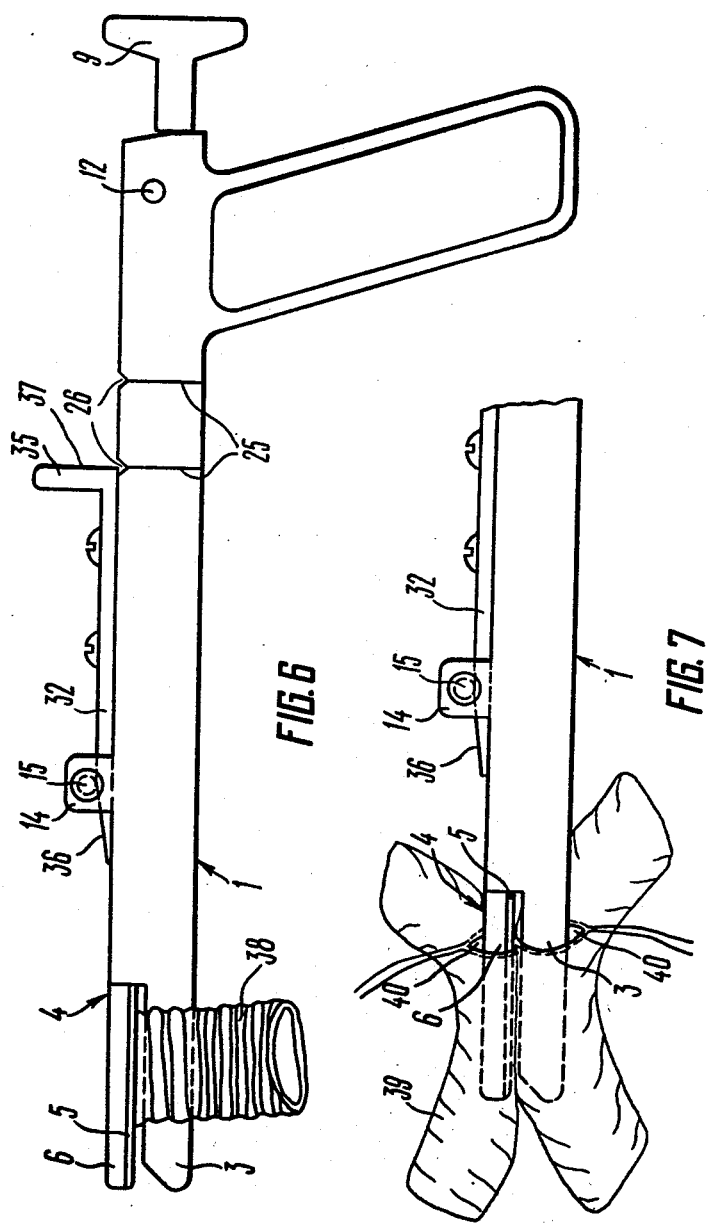

SURGICAL INSTRUMENT FOR APPLYING METAL STAPLES TO ORGANS AND TISSUES AND FOR SIMULTANEOUS DIVISION THEREOF

The present invention relates to medical equipment, and, more specifically, to surgical instruments for suturing organs and tissues with metal staples and simultaneous division therebetween, said instrument being applicable for closing vascular, intestinal, gastric, and bronchial stumps, pulmonary tissue, and other organs. Said instrument can be most expediently employed for applying side-to-side enteroenteroanastomoses, as well as in surgical interventions for occlusions of the main bronchi, for pleural fistulas and empyemas leaving the pleural cavity intact.

There is known an instrument for applying sutures of metal staples to organs and tissues and simultaneous division therebetween that is commonly used for applying gastric anastomoses. (cf. U.S. Pat. No. 3,079,606). Said instrument features an elongated staple inserting jaw and an elongated clinching jaw located alongside thereof. The front operative tip of the staple jaw bears a staple magazine. Said staple magazine contains staple receiving recesses arranged in rows alongside the staple inserting jaw.

Each staple recess contains a staple and a staple driving member with a lug for propelling said staple from the recess.

The anterior operative tip of the clinching jaw bears a detachable staple bending anvil located opposite said staple magazine. The tips of the staples are bent with the aid of grooves located in parallel rows on said anvil alongside the clinching jaw. The location of said grooves corresponds to that of the recesses. The movement of the staple driving members propelling the staples from the recesses of the staple magazine is effected with the aid of an actuating bar provided with a means for moving it alongside the staple inserting jaw.

The side of the actuating bar facing the magazine comprises three parallel plates, two lateral plates having slants facing the magazine intended for engaging with the lugs of the staple driving members in the course of the movement of the actuating bar towards the operative tip of the staple inserting jaw. The middle plate has a rigidly fixed flat knife for severing the organ or tissues between the applied sutures while the actuating bar keeps moving.

The rear end of the staple inserting jaw is pivotally connected with the rear end of the clinching jaw, which ensures the operative tips thereof coming close together and the clinching of the organ or tissues to be sutured between the magazine and the anvil. The needed degree of compression of said organ or tissue permitting suturing thereof without traumatization of the cells of said organ or tissue is ensured by the size of the clearance, i.e. the clearance between the operative surfaces of the magazine and the anvil facing one another. The fixation of the positions of the staple inserting jaw and of the clinching jaw following the closure of the operative tips thereof with a preset clearance between the anvil and the magazine is effected by a mechanism interlocking the staple inserting and the clinching jaws comprising a lever pivotally mounted on the staple inserting jaw and interacting with a pin mounted on the clinching jaw.

The prior art instrument is intended primarily for the application of side-to-side enteroenteroanastomoses and functions in the following way.

One aperture is made on each portion of the intestines to be sutured. The operative tip of the staple inserting jaw is inserted into one aperture, and the operative tip of the clinching jaw into the other aperture. Said jaws are pivotally connected, and by rotation of both jaws the operative tips thereof come together to form the suturing clearance, whereafter the jaws are locked with the aid of the locking mechanism.

The actuating bar with the knife is moved towards the magazine. The slants of the actuating bar engage with the lugs of the staple driving members, longitudinally propelling said staples along the recesses. The driving members eject the staples from the recesses. The staple having left the recess pierces the tissue and, engaging with the anvil, bends to assume a B-shape, thus firmly connecting the tissue.

Simultaneously, the knife severs the tissue between the applied sutures. Following the suturing, the locking mechanism is operated, and the staple inserting and clinching jaws are unlocked, whereafter the jaws are removed from the intestine. Purse-string sutures are applied to the apertures, the suturing of the intestine being thus completed.

However, the rigidly fixed knife, especially a blunted one, drags the tissue being cut and may fail to complete the division. To prevent dragging of the tissue after the knife, the tissue has to be kept in place by being compressed between the faces of the anvil and the magazine or, otherwise, with the aid of staples propelled from the recesses and piercing the tissue somewhat ahead of the knife. Powerful compression, however, results in a destruction of cellular structures of the tissue, causing subsequent incompetence of the suture, and an insufficiently compressed thinned tissue may cause deformity of the unbent tips of the staples when under traction, thus rendering the suture incompetent.

It is an object of the invention to provide a surgical instrument for applying sturures of metal stpales to organs and tissues with simultaneous division therebetween, which would ensure reliable cutting of said organs and tissues without the necessity of holding them tightly between the operative surfaces of the magazine and anvil, or the staples forming the suture.

This object is attained in that in a surgical instrument for applying sutures of metal staples to organs and tissues with simultaneous division thereof, there are an elongated staple inserting jaw with detachable magazines located on the anterior operative tip thereof and containing staple recesses located alongside said staple inserting jaw, staple driving members located in said recesses of the magazines, an acuating bar with means for advancement thereof along said staple inserting jaw, the tip thereof facing said magazine having an inclined camming surface for engaging with said staple driving members in the course of advancing said actuating bar towards the operative tip of said staple inserting jaw, said tip having a knife affixed thereto for severing organs and tissues, an elongated clinching jaw located alongside said staple inserting jaw, the anterior operative tip of said clinching jaw having anvils placed opposite said magazines and having grooves for bending the staples located opposite said recesses for magazine staples, said clinching jaw being rearwardly connected through a pivot with the rear end of said staple inserting jaw resulting, when rotated against one another, in both operative tips coming close together and clamping of the organ or tissue to be sutured therebetween, and a locking mechanism for said staple inserting and clinching jaws. In accordance with the invention, said knife is in the form of a disk with a peripheral cutting edge and is pivotally mounted on to said actuating bar, and the operative tip of said clinching jaw is supplied with a replaceable elastic lining to be adjusted opposite said knife and to interact therewith in cutting.

The proposed surgical instrument ensures reliable division of tissues without preliminary fixation thereof, since they are not entangled in the disk knife during cutting, and, hence, no compression of tissues, to an extent of cellular structures deterioration, is needed. The absence of traction ensures against deformities of the staples.

The invention will be further understood from the following description of exemplary embodiments thereof with reference to the accompanying drawings, wherein:

FIG. 2 is a sectional view taken along line II—II of FIG. 1;

FIG. 3 is a view along arrow III of FIG. 1 of the anterior operative tip of a staple inserting jaw;

FIG. 4 is a sectional view taken along line IV—IV of FIG. 1;

FIG. 5 is a view along arrow V of FIG. 1 of the anterior operative tip of a clinching jaw;

FIG. 6 shows the surgical instrument, in accordance with the invention, in working position in suturing a stump of an organ;

FIG. 7 shows the anterior working tip of the surgical instrument, in accordance with the invention, in applying a side-to-side enteroenteroanastomosis.

Figure 1:
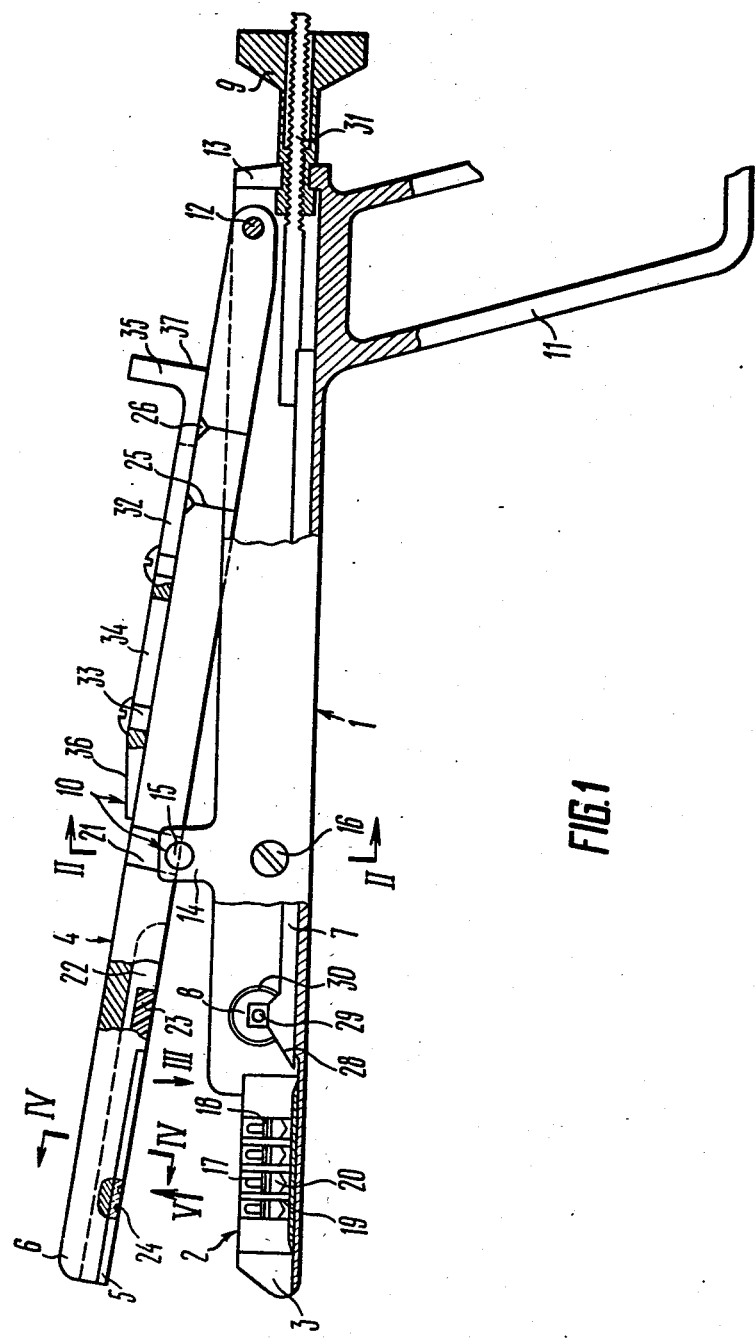
FIG. 1 is a partially sectional schematic view of a surgical instrument for applying sutures of metal staples to organs and tissues with simultaneous division thereof, in accordance with the invention.

Referring now to the drawings, the surgical instrument for the application of sutures of metal staples to organs and tissues with simultaneous division therebetween comprises an elongated staple inserting jaw 1 (FIG. 1) with a detachable staple magazine 2 located on an anterior operative tip 3 of said staple inserting jaw 1, a clinching jaw 4 with an anvil 5 for bending the staples located on an anterior operative tip 6 of said clinching jaw 4, an actuating bar 7 with a knife 8, a wing nut 9 of a means for advancing said actuating bar 7, and a locking mechanism 10 for said staple inserting jaw 1 and clinching jaw 4. The elongated staple inserting jaw 1 (FIGS. 1 and 2) has a trough-shaped section. The rear end of the staple inserting jaw 1 has a handle 11 (FIG. 1) that facilitates the handling of the instrument during surgery, a pivot 12 for pivotally connecting said staple inserting jaw 1 with said clinching jaw 4, and a recess 13 interlocked with a circular fitting in said wing nut 9, which permits free rotation about the axis thereof, but allows no advancement along said staple inserting jaw 1.

The elongated portion of said staple inserting jaw 1 has a lug 14 with pins 15 (FIGS. 1 and 2) of said locking mechanism 10 for said staple inserting jaw 1 and clinching jaw 4, and a screw 16 for preventing transverse displacement of said actuating bar 7 across the staple inserting jaw 1.

The anterior operative tip 3 (FIG. 1) of said staple inserting jaw 1 has a cross-section smaller than the rest of said staple inserting jaw 1, so as to minimize the aperture to be made in the organ in question when the staple inserting jaw 1 is introduced into said organ (e.g. intestine).

The staple magazine 2 has staple recesses 17 each containing a metal U-shaped staple 18 and a staple driving member 19 with a lug 20 (FIGS. 1 and 3). The recesses 17 for the staples 18 are arranged in rows alongside the staple inserting jaw 1.

The staple inserting jaw 1 is pivotally connected at the rear end thereof with the clinching jaw 4 (FIG. 1) by means of a pivot pin 12.

The elongated portion of the clinching jaw 4 has transverse recesses 21 for the passage of the pins 15.

The anterior operative tip 6 of the clinching jaw 4 has a longitudinal recess 22 accommodating an elastic lining 23 (FIGS. 1, 4 and 5), e.g. of polyvinylchloride.

The anvil 5 is fixed on both sides of said recess 22. Said anvil 5 has grooves 24 for bending the tips of U-shaped metal staples 18 (FIG. 1). Said grooves 24 are arranged opposite the recesses 17 for staples 18 in rows alongside the clinching jaw 4 (FIGS. 1 and 5).

For the control of the suturing clearance the staple inserting jaw 1 (FIG. 1) and the clinching jaw 4 contain notch lines 25 and recesses 26, marked with a numerical index that indicates size of the clearance, i.e. the clearance between the magazine 2 and the anvil 5, that permits adequate staple bending.

The trough-shaped staple inserting jaw 1 contains said actuating bar 7 (FIG. 1).

On the tip of the actuating bar 7 facing the magazine 2, there is an inclined camming surface 28 to engage with the lugs 20 of the staple driving members 19, and a knife 8 pivotally connected on a pin 29 somewhat rearwardly of said inclined surface 28.

Said knife 8 is essentially a disk with cutting edges 30 and is adapted to rotate about the pin 29.

On the opposite end of the actuating bar 7, a screw 31 is fixed (FIG. 1) that forms a screw couple with the wing nut 9, this couple serving as a means for advancing said actuating bar 7.

The locking mechanism 10 of the staple inserting jaw 1 and the clinching jaw 4 includes a locking plate 32 fixed to said clinching jaw with screws 33 passing through longitudinal grooves 34 of said locking plate 32, so that said locking plate 32 can move along said clinching jaw 4. To facilitate the advancement of said locking plate 32, a handle 35 is attached thereto. In moving towards the anterior operative tip of said clinching jaw 4, when aligned with said staple inserting jaw 1, the locking plate 32 engages with an inclined camming surface 36 located on the front end thereof, with the pin 15, as depicted in FIGS. 6 and 7, thus effecting the locking of the staple inserting jaw 1 with the clinching jaw 4 while leaving a suturing clearance. The size of the suturing clearance depends on the degree of advancement of said locking plate 32, and is controlled by the position of surface 37 of the handle 35 with reference to the notch lines 25 and recesses 26. The suturing clearance is a variable depending on the height of the staple used, and it is expedient to mark with the aid of the lines 25 the whole permissible range of the suturing clearance, from minimum to maximum.

The surgical instrument for applying sutures of metal staples to organs and tissues with simultaneous division there of functions in the following way.

In the case of closing a stump or an organ 38 (FIG. 6) by suturing, the instrument, in an unlocked position, is attached to said organ 38 so as to place the latter on the anterior operative tip 3 of the staple inserting jaw 1 between magazine 2 and the anvil 5.

In case a side-to-side enteroenteroanastomosis is applied apertures 40 are punctured in the intestinal walls 39 (FIG. 7) and the anterior operative tip 3 of the staple inserting jaw 1 is inserted into one of the apertures 40, and the anterior operative tip 6 of the clinching jaw 4, into the other aperture 40.

Subsequent functioning of the instrument is identical for both closing an organ stump, and for applying side-to-side anastomoses.

The rotation of the clinching jaw 4 and the staple inserting jaw 1 about the axis of pivot 12 (FIG. 6) makes the anterior operative tips 3 and 6 thereof come together and clinch the organ to be sutured 38 or the walls of the intestine 39 (FIG. 7) for the application of an anastomosis. In so doing, the pins 15 are forced to pass along the transverse recesses 21 (FIG. 2) of the clinching jaw 4 and to stop in front of the locking plate 32.

With the aid of the locking mechanism 10, interlocking of the staple inserting jaw 1 with the clinching jaw 4 is achieved, and the suturing clearance is fixed. For this purpose the locking plate 32 is advanced with the aid of the handle 35 (FIG. 6) along the clinching jaw 4 towards the anvil 5, the surface 36 thereof by moving under the pins 15 of the lugs 14 resulting in a further rotation of the staple inserting jaw 1, of the clinching jaw 4, and a further clinching of the organ 38.

The clinching of the organ 38 is continued until the suturing clearance is reached, determined by the position of the surface 37 of the handle 35.

Figure 8:
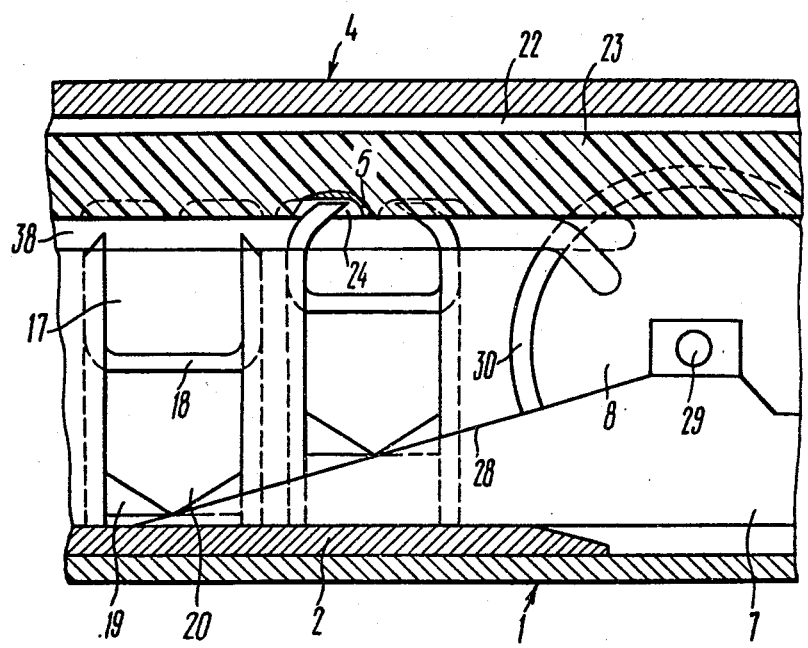
FIG. 8 is a schematic partly sectional view showing suturing and dividing tissues with the surgical instrument, in accordance with the invention.

Following the clinching of the organ 38 to be sutured up to the suturing clearance, by rotation of the wing nut 9, the actuating bar 7 (FIG. 1) is advanced along the staple inserting jaw 1 towards the staple magazine 2. The inclined surface 28 (FIGS. 1 and 8) of the actuating bar 7 then acts upon the lugs 20 of the staple driving members 19, shifting said members along the recesses 17 for staples 18. The staple driving members 19 propel the staples 18 which, after puncturing the tissue with the tips thereof, rest in the grooves 24 against the anvil 5, the staples being bent so as to acquire a B shape, thus firmly connecting the tissue of said organ 38 to be sutured (FIG. 8).

Simultaneously with the advance of actuating bar 7, the disk knife 8 pivotally mounted thereon is also advanced. The disk knife 8 penetrates with the cutting edge 30 thereof into the elastic lining 23, and begins revolving owing to the friction between said knife 8 and elastic lining 23. The rotation of the disk knife 8 ensures against entangling of the tissue therein, and, instead, rolls over the tissue, pressing it to the elastic lining 23. Since the knife 8 partially cuts into the elastic lining 23, the severing of the tissue is reliably achieved.

Upon completing the suturing, the instrument is opened by returning the locking plate 32 (FIG. 1) into the initial position thereof and removed from the organ being sutured.

The actuating bar 7 may be returned to the initial position prior to removing the instrument, or following such removal, as preferred by the surgeon, and as prompted by the desire to accelerate the procedure. The instrument applies two sutures one to the part to be removed and one to the remaining part of the organ or tissue divided between the sutures.

The employment of the disk knife 8 interacting with the elastic lining 23 increases the reliability of the cutting of the tissue. The disk knife 8 is not entangled in the tissue, which avoid considerable compressing efforts for retaining the tissue in place, thus decreasing the hazard of destroying the cellular tissues and of the possible subsequent incompetence of the sutures.

The tissue, when free of traction, causes no deformity of the tips of the staples 18, which improves the quality of the staple suture.

The reliable guaranteed division of the tissue along the elastic lining 23 permits the instrument to be employed in narrow and deep wounds and in poorly accessible sites, e.g. in cases of pulmonary occlusions without incising the pleural cavity.

Besides, the instrument can be used for dividing the tissues without suturing thereof. As test trials have demosntrated, even without compression the tissue is securely divided by the disk knife 8.

The elastic lining 23 is disposable and replaceable. It is substituted after every suturing procedure. Its replacement is simple and convenient, since it is retained in the recess 22 of the anterior operative tip 6 of the clinching jaw 4 by friction alone.

Thus, the structure of the invention provides an elongated staple-inserting means 1 and an elongated clinching means 4. The pivot 12 forms a connecting means operatively connected with the means 1 and 4 for interconnecting the means 1 and 4 for movement one with respect to the other to and from an operating position where the distance between the means 1 and 4 is sufficient for clamping tissue between the means 1 and 4 with a given pressure. The staple-inserting means 1 carries in recesses thereof the two rows of staple-driving members 19 for movement toward the clinching means 4, these members 19 being adapted to engage staples which are to be driven toward the clinching means 4 while the latter has in alignment with the rows of driving members 19 the elongated anvil members 5 which cooperate with the staples to bend the tips thereof after these tips penetrate through the tissue, as described above. The elongated bar 7 forms an actuating means movably carried by the staple-inserting means 1 for movement therealong to displace the members 19, by engaging the lugs 20 thereof with the inclined camming surface 28, this elongated actuating means 7 being driven by way of a drive means formed by the screw 31 which is fixed to the bar 7 and the rotary wing nut 9. The lock means 10 together with the pins 15 forms a means for releasably locking the pair of means 1 and 4 in a predetermined operative position where the means 1 and 4 are situated at a predetermined distance from each other to provide the desirable clamping action on the tissue. This lock means 10 includes an adjusting means formed by the inclined camming surface 36 which is capable of adjusting the distance at which the pair of means 1 and 4 are locked with respect to each other, so that in this way the clamping pressure on the tissue can be adjusted.

The elongated actuating means 7 of course supports for rotary movement the cutting disk 8 which is provided with the peripheral cutting edge 30, this disk 8 being supported for rotary movement by the actuating means 7 at a location according to which the disk 8 can travel between the rows of driving members 19. The elongated clinching means 4 frictionally carries in a suitable recess between the pair of anvil members 5 the elongated elastic member 23 into which the cutting edge of the disk 8 penetrates to achieve a clean cutting action. This clean cutting action, without any undesirable dragging or bunching of the tissue, is achieved because of a number of operative factors. These factors include in the first place the fact that the knife 8 will rotate as a result of its frictional engagement with the elongated elastic member 23. The direction of rotation of the disk 8 which is achieved during advance of the means 7 is such that the disk urges the tissue toward the elastic member 23 and cuts cleanly through the tissue while penetrating into the elastic member 23. Furthermore, a factor contributing to the clean cutting action resides in the action of the elastic member 23 which immediately after being penetrated by the knife 8 expands to displace itself along the knife 8 toward the pivot 29 so that in this way a clean slicing action on the tissue is achieved by way of the rotary knife 8. This highly effective cutting action is enhanced by the precise clamping of the tissue achieved by way of the adjusting means for adjusting the locking means 10 as well as by the drive means 9, 31, which is available to the operator for advancing the means 7 forwardly along the cutting stroke in a smooth manner.

What is claimed is:

1. In a surgical instrument for suturing and dividing tissue, a pair of means one of which is an elongated staple-inserting means and the other of which is an elongated clinching means, connecting means operatively connected with said pair of means for interconnecting them for movement one with respect to the other to and from an operative position where the staple-inserting means and clinching means clamp between themselves tissue which is to be operated on, said staple-inserting means carrying two rows of staple-driving members for driving staples toward said clinching means while the latter carries in alignment with said rows of staple-driving members a pair of anvil members for engaging the tips of the driven staples after they penetrate through the tissue and for bending said tips, said rows of staple-driving members defining between themselves a space having a given length and said clinching means carrying between said anvil members an elongated elastic member aligned with and being at least as long as said space while having a surface directed toward said space when said pair of means are in said operative position thereof, elongated actuating means supported by said staple-inserting means for movement in a given direction therealong to displace said staple-driving members toward said clinching means, and a rotary knife disk supported by said elongated acutating means for rotation about an axis extending centrally through and being perpendicular to said disk while also extending transversely with respect to said given direction, with said disk being situated at a location where said disk will move with said actuating means along said space between said rows of staple-driving members while said disk has a diameter great enough for penetrating at an outer peripheral cutting edge of said disk into said elastic member which is situated between said anvil members, said disk having only a relatively small portion of said peripheral cutting edge penetrating into said elastic member at any given instant and said disk rotating in response to frictional engagement with said elastic member while travelling along and penetrating into the latter for progressively cutting with a slicing action cleanly through tissue clamped between said pair of means.

2. The combination of claim 1 including a releasable lock means operatively connected with said pair of means for releasably locking them to each other in said operative position and wherein an adjusting means is operatively connected with said releasable lock means for adjusting the latter to lock said pair of means at a distance from each other which will provide a predetermined clamping pressure on tissue clamped between said pair of means.

3. The combination of claim 2 and wherein said lock means and adjusting means include at least one pin fixed to one of said pair of means and a shiftable bar movably carried by the other of said pair of means and having an inclined claming surface for engaging said pin, the extent to which said inclined camming surface is moved with respect to said pin adjusting the distance between said pair of means.

4. The combination of claim 1 and wherein a drive means is operatively connected with said actuating means for moving the latter to displace said staple-driving members toward said clinching means and to move said disk with said acutating means.

5. The combination of claim 4 and wherein said drive means includes an elongated screw fixed to said actuating means and a rotary nut supported for rotation by said staple-inserting means and cooperating with said screw for advancing the latter together with said actuating means.

6. The combination of claim 1 and wherein said clinching means is formed between said pair of anvil members with a recess in which said elastic member is frictionally retained so that said elastic member can readily be removed and replaced by another elastic member.

7. The combination of claim 1 and wherein said actuating means has a front portion situated in advance of said disk when moving in said given direction for engaging and displacing said staple-driving members toward said clinching means.

* * * * *